United States Patent
Pirazzoli et al.

(10) Patent No.: US 7,131,956 B1
(45) Date of Patent: Nov. 7, 2006

(54) DIALYSIS MACHINE AND METHOD OF CONTROLLING IT

(75) Inventors: Paolo Pirazzoli, San Prospero (IT); Antonio Bosetto, Mirandolla (IT); Francesco Paolini, Ganaceto (IT)

(73) Assignee: Gambro Hospal Schweiz AG, Basel (CH)

(*) Notice: Subject to any disclaimer, the term of this patent is extended or adjusted under 35 U.S.C. 154(b) by 1218 days.

(21) Appl. No.: 09/787,624

(22) PCT Filed: Jul. 28, 2000

(86) PCT No.: PCT/IB00/01069

§ 371 (c)(1),
(2), (4) Date: Jul. 15, 2003

(87) PCT Pub. No.: WO01/08723

PCT Pub. Date: Feb. 8, 2001

(30) Foreign Application Priority Data

Jul. 30, 1999 (IT) ............................... TO99A0680

(51) Int. Cl.
*A61M 37/00* (2006.01)
*C02F 1/44* (2006.01)
*C02F 1/00* (2006.01)
*B01D 35/14* (2006.01)
*A31M 1/36* (2006.01)

(52) U.S. Cl. .................. 604/6.09; 604/4.01; 604/5.01; 604/5.04; 604/6.11; 210/739; 210/85; 210/645; 210/646; 210/650; 422/44

(58) Field of Classification Search ............... 604/4.01, 604/5.01, 5.04, 6.09, 6.11; 210/600, 634, 210/644–646, 739–746, 195.2, 203, 321.6, 210/321.71, 416.1, 433.1, 85, 97, 143, 650; 422/44–48

See application file for complete search history.

(56) References Cited

U.S. PATENT DOCUMENTS

| | | | |
|---|---|---|---|
| 5,366,630 A | 11/1994 | Chevallet | 210/645 |
| 5,401,238 A | 3/1995 | Pirazzoli | 604/4 |
| 5,702,597 A * | 12/1997 | Chevallet et al. | 210/195.2 |
| 5,762,805 A * | 6/1998 | Truitt et al. | 210/645 |
| 5,954,951 A * | 9/1999 | Nuccio | 210/87 |
| 6,471,872 B1 * | 10/2002 | Kitaevich et al. | 210/739 |
| 6,730,233 B1 * | 5/2004 | Pedrazzi | 210/739 |
| 6,966,979 B1 * | 11/2005 | Pedrazzi | 210/85 |

FOREIGN PATENT DOCUMENTS

DE 4024434 2/1992

OTHER PUBLICATIONS

Noma Kohei, "Controller for Blood Pump", Patent Abstracts of Japan of JP 07 265416, (Oct. 17, 1995).

* cited by examiner

*Primary Examiner*—Tatyana Zalukaeva
*Assistant Examiner*—Leslie R. Deak
(74) *Attorney, Agent, or Firm*—Finnegan, Henderson, Farabow, Garrett & Dunner, L.L.P.

(57) ABSTRACT

A dialysis machine comprises: means for calculating (60) a filtration factor (FF) as a function of the ultrafiltration rate (UFR) and of a plasma flow rate ($Q_p$); first comparison means (65) for comparing the filtration factor (FF) with a limit value of admissibility; and signaling means (70) for generating a signal (A) indicating the result of the comparison.

17 Claims, 2 Drawing Sheets

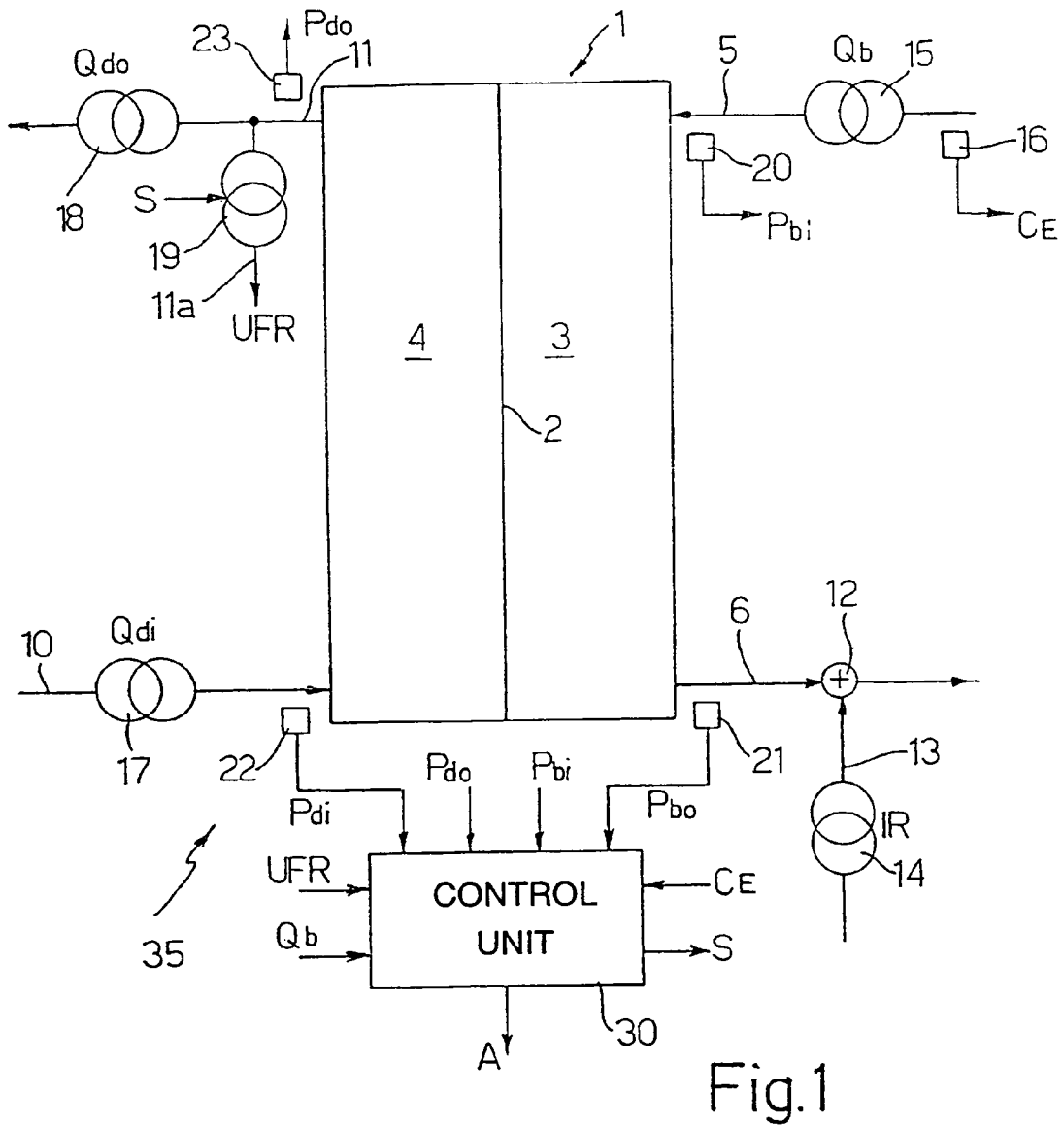
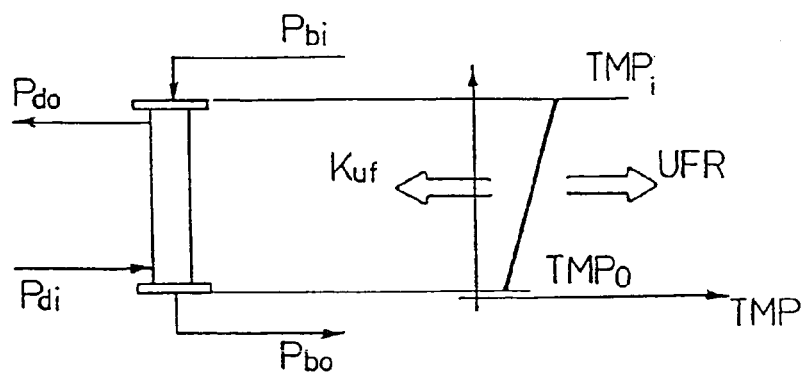

DIALYSIS MACHINE AND METHOD OF CONTROLLING IT

The present invention relates to a dialysis machine and a method for controlling it.

As is well known, blood is composed of a liquid part called blood plasma and a cellular part formed by the cells of the blood itself, including red blood cells (erythrocytes) among others; moreover, in cases of renal insufficiency, the blood also contains an excess of substances of low molecular weight (also called solute hereinafter) which must be eliminated by dialysis treatment effected by means of a dialysis machine.

A conventional dialysis machine includes a filter consisting of a blood compartment and a dialysing compartment, separated from each other by a semipermeable membrane; in use, the blood to be treated and the dialysis fluid pass through these respective compartments, generally in counterflow.

For better understanding, reference is made to FIG. 1, showing schematically a part of a dialysis machine 35, comprising a filter 1 equipped with a membrane 2 that divides filter 1 into a blood compartment 3 and a dialysing compartment 4. An arterial line 5 and a venous line 6 are connected to an inlet and, respectively, an outlet of blood compartment 6. A dialysis fluid inlet line 10 and a dialysis fluid outlet line 11 are connected to an inlet and, respectively, an outlet of dialysing compartment 4.

During dialysis treatment, the undesirable substances present in the blood migrate from the blood compartment 3 to the dialysing compartment 4 through membrane 2 either by diffusion or by convection, owing to the passage of a proportion of the liquid present in the blood towards the dialysing compartment. Accordingly, at the end of the dialytic procedure, the patient's weight will have decreased.

To improve the efficiency of dialysis treatment, techniques of ultrafiltration are also known, whereby a large quantity of plasma fluid is removed, so as to increase the effects of transport of the undesired substances by convection. The quantity of plasma fluid removed in excess relative to the desired final weight loss is infused into the patient as a substitution liquid, either before passage of the blood through the filter (pre-dilution technique) or after the filter (post-dilution technique).

Both techniques have their advantages and disadvantages. In particular, the post-dilution technique, to which reference will be made hereinafter though without loss of generality, offers the advantage of improving the efficiency of dialysis, since the fluid removed through the filter is more concentrated compared with the pre-dilution technique and so, at equal flows, it provides greater diffusive efficiency, but it has some critical aspects. Thus, with post-dilution it is easier for values of haemoconcentration to be reached in the filter which hamper both flow and ultrafiltration (through partial blocking of the filter), giving rise to the phenomenon of "caking". Consequently, a more limited amount of plasma fluid can be extracted with the post-dilution technique than the pre-dilution technique.

The dialysis machine 35 in FIG. 1, which employs a post-dilution technique, therefore includes a summation node 12 connected to the venous line 6 and to an infusion line 13 in which an infusion pump 14 is installed, and its delivery IR determines the amount of fluid infused. For completeness, FIG. 1 also shows a blood pump 15, located on the arterial line 5, whose delivery $Q_b$ determines the volume of blood submitted to dialysis treatment; a haemoconcentration sensor 16, arranged along the arterial line 5 and generating at its output a haemoconcentration signal $C_E$; an inlet dialysing pump 17, positioned on the dialysis fluid inlet line 10 and supplying a flow rate $Q_{di}$; an outlet dialysing pump 18, positioned on the dialysis fluid outlet line 11 and supplying a flow rate $Q_{do}$; an ultrafiltration pump 19, positioned on a branch line 11a connected to the dialysis fluid outlet line 11 and supplying a flow rate UFR; and four pressure sensors 20–23, arranged respectively on the arterial line 5, the venous line 6, the dialysis fluid inlet line 10 and the dialysis fluid outlet line 11 and supplying the pressures $P_{bi}$, $P_{bo}$, $P_{di}$, $P_{do}$ respectively.

In a manner that is not shown, flowmeters for monitoring and if necessary controlling pumps 15, 17, 18 and 19 respectively can be provided on the arterial line 5, on the dialysis fluid inlet line 10 and dialysis fluid outlet line 11, and on the branch line 11a.

In a known manner, the blood flow $Q_b$ is set by the operator; in addition, preferably the required weight loss WLR and the reinfusion IR are set by the operator and the dialysis machine 35 determines the ultrafiltration UFR, as the sum of WLR and IR. Alternatively, the operator can set the ultrafiltration UFR and the required weight loss WLR and the machine determines the reinfusion IR. Furthermore, the dialysis machine controls the dialysis fluid outlet flow $Q_{do}$ and keeps it equal to the dialysis fluid inlet flow $Q_{di}$, to keep the flows in balance.

As an alternative to what has been described, the ultrafiltration pump 19 may be absent and the pump 18 on the dialysis fluid outlet line 11 is controlled to give a flow equal to the sum of the flow $Q_{di}$ of the inlet dialysing pump 17 and of the ultrafiltration UFR. Finally, other solutions exist, which for conciseness are not described, for controlling ultrafiltration, based for example on pressure differentials.

A control unit 30 receives the signals generated by the various sensors present, such as the haemoconcentration CE, the pressure signals $P_{bi}$, $P_{bo}$, $P_{di}$, $P_{do}$, as well as signals monitoring the set quantities, such as blood flow $Q_b$, the dialysis fluid inlet $Q_{di}$ and dialysis fluid outlet $Q_{do}$ flow and the ultrafiltration UFR, for controlling the operation of the dialysis machine 35.

An important parameter for monitoring the conditions of the filter and avoiding the aforementioned problems of restriction of flow and of ultrafiltration, is the transmembrane value, i.e. the pressure differential between the two sides (blood and dialysis fluid) of the filter. In particular, the static and dynamic components of the pressure drop in the filter mean that ultrafiltration (measured as ultrafiltration per hour or Ultra Filtration Rate UFR), by increasing the concentration of the blood, produces a general increase in pressure along the whole longitudinal dimension of filter 1, as indicated by the arrow pointing to the right in FIG. 2, causing an increase both of the inlet transmembrane value (relative to the blood flow), indicated by $TMP_i$ and equal to $P_{bi}-P_{do}$, and of the outlet transmembrane value, indicated by $TMP_o$ and equal to $P_{bo}-P_{di}$.

For increasing the efficiency of dialysis by increasing convection, it is found to be advantageous to use filters characterized by high permeability $K_{uf}$, so as to cause a leftward shift of the transmembrane curve. On the other hand, high permeability in conditions of low ultrafiltration can give rise to phenomena of reverse flow ("backfiltration"), which might cause problems of contamination of the blood and hypersensitization of the patient and must therefore be avoided.

Accordingly, it has already been proposed to monitor the transmembrane value of filter 1 and to regulate the blood flow $Q_b$ and the ultrafiltration UFR so as to keep this transmembrane value within acceptable limits.

Although such a solution makes it possible to point out and eliminate some critical aspects of the system, this is still not sufficient to always guarantee safe conditions of dialysis and increased efficiency.

In particular, as the values of transmembrane pressure are linked only indirectly to the controllable quantities (blood flow and ultrafiltration), regulation of these quantities on the basis of the transmembrane pressure is not immediate but requires successive adjustments. Moreover, monitoring of the transmembrane values does not provide timely and unambiguous information regarding the phenomenon of caking.

The aim of the present invention is to provide a method of control that solves the problem described above.

According to the present invention, a method is provided for controlling a dialysis machine comprising:

a filter having a first and a second compartments separated by a semi-permeable membrane;
a first circuit connected to the first compartment for a liquid including a liquid component, a cellular component that is retained by the membrane and solutes that pass through the membrane;
a second circuit connected to the second compartment for a dialysis fluid;
means for circulating the liquid to be filtered in the first circuit at an inlet flow upstream of the filter;
means for causing a controlled flow of the liquid component and of the solutes through the membrane, the method comprising the following steps:

circulating the liquid to be filtered in the first compartment of the filter;
causing a controlled flow of the liquid component and of the solutes through the membrane;
determining a value of a first and a second parameters (UFR, $Q_p$) correlated respectively with the controlled flow of the liquid component through the membrane and with the flow of the liquid component at the inlet of the first compartment;
calculating a filtration factor (FF) as a function of the value of the first and second parameters (UFR, $Q_p$);
checking whether the filtration factor (FF) has a predetermined relation with a limit value of admissibility;
generating a signal indicating the result of the verification.

According to the invention, a dialysis machine is further provided for the treatment of a liquid to be filtered, comprising a liquid component, a cellular component and solutes, the machine comprising:

a filter having a first and a second compartment separated by a semi-permeable membrane;
a first circuit for the liquid to be filtered, comprising a liquid inlet line connected to an inlet of the first compartment and a liquid outlet line connected to an outlet of the first compartment;
a second circuit for a dialysis fluid comprising a dialysis liquid inlet line connected to an inlet of the second compartment and a dialysis liquid outlet line connected to an outlet of the second compartment;
first pumping means connected to the first circuit for circulating the liquid to be filtered through the first compartment;
second pumping means connected to the second circuit for circulating a dialysis fluid in the second compartment and for causing a flow of part of the liquid component and of the solutes through the membrane;
means for detecting the value of a first parameter correlated with the controlled flow of the liquid component through the membrane and the value of a second parameter correlated with the flow of the liquid component at the inlet of the filter;
first means for calculating a filtration factor FF as a function of the value of the first and second parameters;
first comparison means for comparing the filtration factor (FF) with a limit value of admissibility; and
signaling means for generating a signal (A) indicating the result of the comparison.

For better understanding of the present invention, a first embodiment thereof will now be described, purely as a non-limitative example, referring to the accompanying drawings, in which:

FIG. 1 shows a simplified equivalent diagram of a known dialysis machine;

FIG. 2 shows the variation of the pressures on the filter in FIG. 1;

Figure 3:
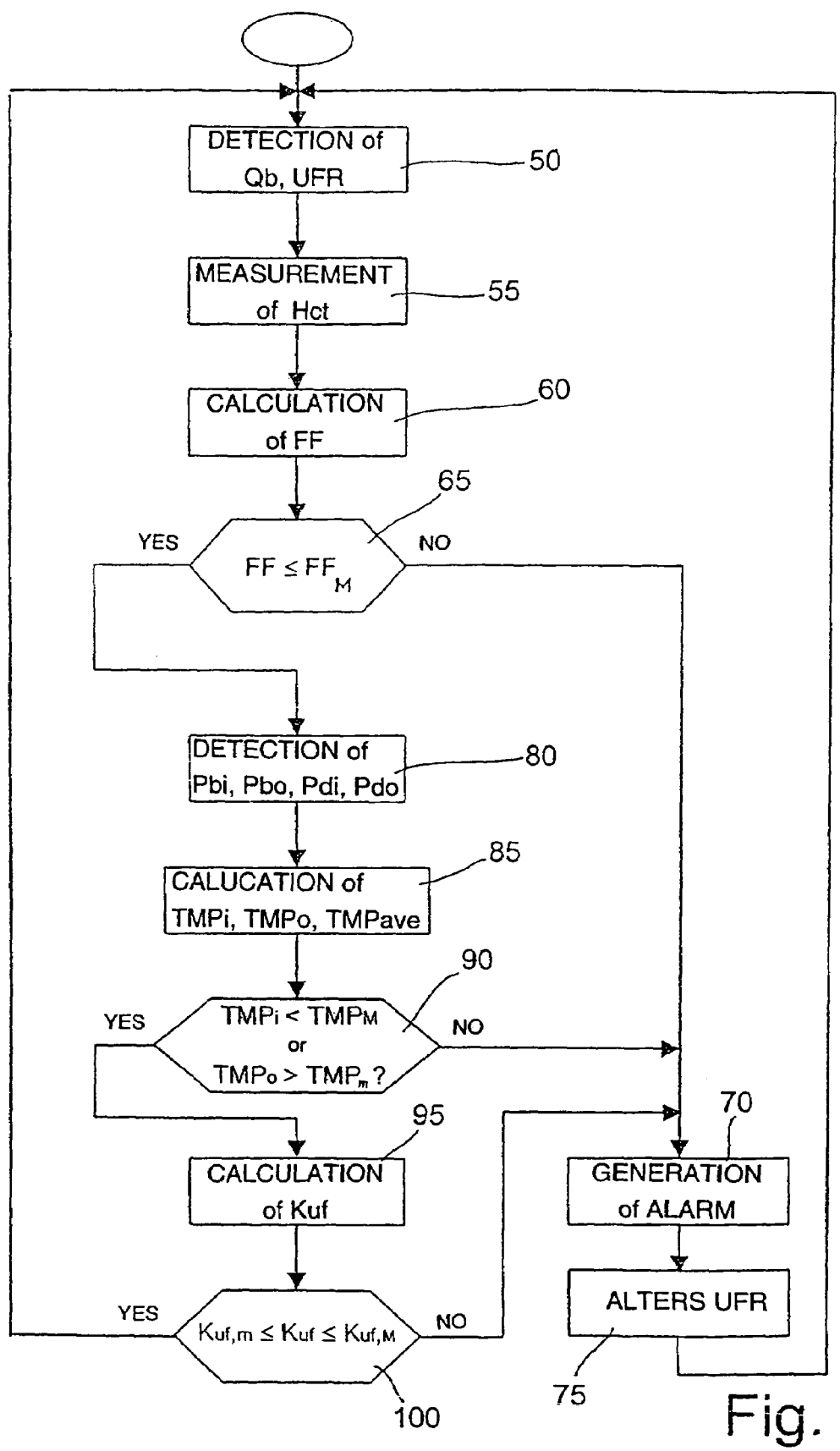
FIG. 3 shows a flow diagram relating to one embodiment of the present method.

The invention is based on studies undertaken by the applicant, which showed that the occurrence or non-occurrence of critical conditions does not depend on the absolute value of the individual parameters under control, but on a relation between the amount of liquid removed by ultrafiltration and the plasma flow at the filter inlet.

Accordingly, since the plasma flow depends on the blood flow $Q_b$ and on the initial concentration of the blood, according to one embodiment of the invention, the data acquired are the blood flow $Q_b$, the ultrafiltration UFR and the blood concentration; the filtration factor FF defined hereunder is determined on the basis of these quantities:

$$FF = UFR/Q_p = UFR/[Q_b(1-Hct)]$$

in which $Q_p$ is the plasma flow and Hct is the haematocrit, i.e. the concentration of red blood cells in the arterial blood; this is followed by verification of whether the filtration factor FF is within an admissible range and, if not, a warning signal is generated and an inlet quantity, preferably the ultrafiltration, is altered so as to return the system to a non-critical operating point.

This control situation is shown schematically in FIG. 1 by a control signal S generated by the control unit 30 and acting on the ultrafiltration pump 19 and by a signal A supplied to a display unit and/or an acoustic signalling element.

Control of the operating point of filter 1 also permits its optimization; specifically, in the case of increased deviation between the calculated filtration factor FF and the maximum limit set (for example in the case of previous reduction of ultrafiltration), the operating conditions can be modified so as to increase the efficiency of filtration, in particular by increasing the ultrafiltration. This makes it possible to modify the operating conditions of the filter dynamically during the treatment, following any variations and fluctuations of the haematocrit in the course of treatment, to obtain conditions of safety and increased efficiency at every instant.

The concentration of the blood can be measured directly, from the haematocrit Hct, or indirectly via measurement of haemoglobin (in which case the value of the haematocrit Hct is obtained by dividing the measured haemoglobin value Hgb by the haemoglobin cellular mean concentration (Hcmc) or via measurements of the viscosity, electrical conductivity or density of the blood, in a known way which will not be described in detail.

Advantageously, measurements are also taken of the four pressures on the inlet and outlet sides both of the blood and of the dialysis fluid, and the inlet and outlet transmembrane value, or the average value $TMP_{ave}=(TMP_i-TMP_o)/2$, is also monitored.

Preferably, the actual permeability of the membrane, defined hereunder, is also calculated:

$$K_{uf}=UFR/TMP_{ave}.$$

In both cases, if the inlet and outlet transmembrane value or its average value and/or the actual permeability exhibit inadmissible values, warnings are generated and ultrafiltration is adjusted so as to return the controlled quantities to within acceptable limits. In dangerous conditions, in general a stop condition is provided for the dialysis machine.

An example of the present method will now be described with reference to FIG. 3, which shows a flow diagram.

During dialysis treatment, block 50, control unit 30 receives the blood flow value $Q_b$ (set by the operator) and the ultrafiltration value UFR (which, as noted above, is equal to the sum of the weight loss per hour WLR (Weight Loss Rate) and the infusion rate IR, both of which are generally set by the operator; alternatively, the ultrafiltration UFR and the weight loss rate WLR can be set by the operator directly, and the machine determines the infusion rate IR); then, on the basis of the concentration signal $C_E$ (for example indicating haemoglobin Hgb) supplied by sensor 16, the haematocrit Hct is determined, block 55.

Then, block 60, control unit 30 calculates the filtration factor $FF=UFR/[Q_b(1-Hct)]$; and, block 65, checks whether this is below an upper limit $FF_M$. For example, the maximum value may be equal to 50%, and if this is exceeded this is a sign of danger through excessive haemoconcentration in the filter.

If the filtration factor FF does not have an acceptable value (output NO from block 65), control unit 30 generates the warning signal A, block 70, and alters the ultrafiltration UFR via pump UFR 19 so as to return the filtration factor FF to an acceptable value, block 75. Preferably, for this purpose a control system of the PID type is used, the parameters of which are adjusted at the calibration step, in a known manner which is not described in detail. Consequently, the machine also makes a corresponding change to the infusion rate IR supplied by pump 14, so as to keep the weight loss WLR constant.

Then control unit 30 returns to acquisition of $Q_b$, UFR and Hct, blocks 50, 55.

If the value of the filtration factor FF is acceptable (output YES from block 65), control unit 30 can check whether the ultrafiltration factor can be incremented to increase efficiency in conditions of safety (in a manner that is not shown) and then acquires the values of the inlet and outlet pressure on the blood side and the dialysis fluid side, $P_{bi}, P_{bo}, P_{di}, P_{do}$, block 80. Typically, these values are supplied directly by the four sensors 20–23 provided on the dialysis machine, as shown in FIG. 1.

Then, block 85, control unit 30 calculates the inlet $TMP_i$, outlet $TMP_o$, and average $TMP_{ave}$ transmembrane values, as described above, and at least checks whether the inlet transmembrane value $TMP_i$ is less than an upper limit $TMP_M$ and whether the outlet transmembrane value $TMP_o$ is greater than a lower limit $TMP_m$, block 90. For example, the lower limit $TMP_m$ can be equal to 20 mmHg, and indicates risk of return flow ("backfiltration"), whereas the upper limit $TMP_M$ can be equal to 300–500 mmHg, and indicates risk of degassing and failure of the filter, with problems in the operation of the dialysis machine.

If the inlet transmembrane value $TMP_i$ or the outlet transmembrane value $TMP_o$ does not satisfy the conditions indicated, output NO from block 90, an alarm is generated and the ultrafiltration value is altered, as described above with reference to blocks 70, 75; on the other hand, if the outlet transmembrane value $TMP_o$ is acceptable, control unit 30 calculates, in the manner described above, the actual permeability of the membrane $K_{uf}$, block 95.

Finally, there is a check as to whether the actual permeability of the membrane $K_{uf}$ is within an admissible range defined by a minimum value $K_{uf,m}$ and a maximum value $K_{uf,M}$, block 100. For example, the thresholds of admissibility $K_{uf,m}$ can be equal to 5 and, respectively, 100 (ml/min)/mmHg, indicating problems with the membrane (for example breakage or clogging of the membrane). If negative, an alarm is again generated and the ultrafiltration is altered (blocks 70, 75), but if positive (output YES from block 100), control unit 35 repeats the steps necessary for controlling the filtration factor, returning to block 50.

The advantages of the present method are clear from the above description. It is emphasized in particular that the present method permits timely indication of dangerous conditions connected with longitudinal caking of the filter so that preventive steps can be taken. Moreover, since the present method is based on monitoring of a quantity that is directly correlated with the operating conditions of the filter, this immediately supplies the extent of the changes required, or in any case greatly simplifies determination of these changes, for the purpose of improving the efficiency of filtration and avoiding critical situations. Moreover, the present method does not require modification of the dialysis machine, since the control unit 30 can be implemented by the unit, already provided, for controlling the dialysis treatment and the quantities used are already available or can easily be obtained by mathematical methods from the quantities that are measured or set.

Finally, it is clear that the method and the dialysis machine described and illustrated here can be modified and varied without leaving the protective scope of the present invention, as defined in the accompanying claims.

The invention claimed is:

1. A method for controlling a dialysis machine comprising the following steps:
   providing a filter having a first and a second compartment separated by a semi-permeable membrane;
   connecting to the first compartment a first circuit for a liquid, said liquid including a liquid component, a cellular component that is retained by the membrane, and solutes that pass through the membrane;
   connecting to the second compartment a second circuit for a dialysis fluid;
   circulating the liquid to be filtered in the first compartment of the filter;
   causing a controlled flow of the liquid component and of the solutes through the membrane;
   determining a value of a first parameter correlated with the controlled flow of the liquid component through the membrane;
   determining a value of a second parameter correlated with the flow of the liquid component at an inlet of the first compartment, said second parameter being at least one selected in the group comprising: hematocrit, hemoglobin, blood viscosity, blood electrical conductivity, and blood density;
   calculating a filtration factor as a function of the value of the first and second parameters; and controlling the flow of the liquid component through the membrane or an inlet flow of the liquid to be filtered as a function of the filtration factor.

2. A method according to claim 1, further comprising the steps of:
checking whether the filtration factor has a predetermined relation with a limit value of admissibility; and
generating a signal indicating the result of the verification.

3. A method according to claim 1, wherein the first parameter is an ultrafiltration rate and the second parameter is a plasma flow rate.

4. A method according to claim 3, wherein the step of determining the value of a second parameter comprises the sub-steps of:
determining an inlet flow rate of the liquid to be filtered; and
determining the concentration of the cellular component in the inlet liquid, the calculation step comprising the calculation of the filtration factor according to the formula:

$$FF=UFR/[Qb(1-Hct)]$$

where FF is the filtration factor, UFR is the ultrafiltration rate, Qb is the inlet flow rate of the liquid to be filtered, and Hct is the concentration of the cellular component in the inlet liquid.

5. A method according to claim 4, wherein the checking step comprises checking whether the filtration factor is below a predetermined maximum threshold value.

6. A method according to claim 4 or 5, wherein the step of determining the concentration of the cellular component comprises measuring a hemoglobin value and dividing the hemoglobin value by a constant coefficient.

7. A method according to claim 1, further comprising the steps:
detecting pressure values at the inlet of the first compartment and an outlet of the first compartment and pressure values at an inlet and an outlet of the second compartment;
calculating an inlet transmembrane value as the difference between the pressure value at the inlet of the first compartment and the pressure value at the outlet of the second compartment and an outlet transmembrane value as the difference between the pressure value at the outlet of the first compartment and the pressure value at the inlet of the second compartment;
checking whether the inlet and outlet transmembrane values satisfy predetermined relations with respective threshold values; and
generating a signal indicating the result of the checking step.

8. A method according to claim 1, further comprising the steps of:
detecting pressure values at the inlet of the first compartment and an outlet of the first compartment and pressure values at an inlet and an outlet of the second compartment;
calculating an inlet transmembrane value as the difference between the pressure value at the inlet of the first compartment and the pressure value at the outlet of the second compartment and an outlet transmembrane value as the difference between the pressure value at the outlet of the first compartment and the pressure value at the inlet of the second compartment;
calculating an average transmembrane value between the inlet transmembrane value and the outlet transmembrane value;

calculating a value of the actual permeability as the ratio of the value of the first parameter to the average transmembrane value;
checking whether the actual permeability value satisfies a respective predetermined relation with respect to threshold values; and
generating a signal indicating the result of the checking step.

9. A dialysis machine for treatment of a liquid to be filtered, comprising a liquid component, a cellular component and solutes, the machine comprising:
a filter having a first and a second compartment separated by a semi-permeable membrane;
a first circuit for the liquid to be filtered, comprising a liquid inlet line connected to an inlet of the first compartment and a liquid outlet line connected to an outlet of the first compartment;
a second circuit for a dialysis fluid comprising a dialysis liquid inlet line connected to an inlet of the second compartment and a dialysis liquid outlet line connected to an outlet of the second compartment;
a first pumping apparatus connected to the first circuit for circulating the liquid to be filtered through the first compartment;
a second pumping apparatus connected to the second circuit for circulating a dialysis fluid in the second compartment and for causing a flow of part of the liquid component and of the solutes through the membrane;
a detector configured to detect the value of a first parameter correlated with the controlled flow of the liquid component through the membrane and configured to detect the value of a second parameter correlated with the flow of the liquid component at the inlet of the filter, said second parameter being at least one selected from the group comprising: hematocrit, hemoglobin, blood viscosity, blood electrical conductivity, and blood density;
a first calculator programmed to calculate a filtration factor as a function of the value of the first and second parameters; and
a first controller programmed to control the flow of the liquid component through the membrane or the inlet flow of the liquid to be filtered as a function of the filtration factor.

10. A dialysis machine according to claim 9, further comprising:
a first comparing device programmed to compare the filtration factor with a limit value of admissibility; and
a signaling device programmed to generate a signal indicating the result of the comparison.

11. A dialysis machine according to claim 9 wherein the first parameter is a rate of ultrafiltration and the second parameter is a plasma flow rate.

12. A dialysis machine according to claim 9, wherein the detector detects the flow rate of the liquid circulated by the first pumping apparatus and a measurement device configured to measure the concentration of the cellular component, and said first calculator calculates the filtration factor according to the formula:

$$FF=UFR/[Qb(1-Hct)]$$

where FF is the filtration factor, UFR is the ultrafiltration rate, Qb is the inlet flow rate of the liquid to be filtered, and Hct is the concentration of the cellular component in the inlet liquid.

13. A dialysis machine according to claim 9 further comprising:
- a first, a second, a third and a fourth pressure sensor arranged respectively on the liquid inlet line, on the liquid outlet line, on the dialysis fluid inlet line and on the dialysis fluid outlet line for generating, respectively, a first, a second, a third and a fourth pressure value;
- a second calculator programmed to calculate an inlet transmembrane value as the difference between the first and fourth pressure values and an outlet transmembrane value as the difference between the second and third pressure values;
- a comparing device programmed to compare the inlet and outlet transmembrane values with respective threshold values;
- and a second controller programmed to control the first pumping apparatus and the second pumping apparatus and configured to alter one of the inlet flow of the liquid to be filtered or of the controlled flow of the liquid component through the membrane when the inlet and outlet transmembrane values do not have permissible values.

14. A dialysis machine according to claim 9 further comprising:
- a first, a second, a third and a fourth pressure sensor arranged respectively on the liquid inlet line, on the liquid outlet line, on the dialysis fluid inlet line and on the dialysis fluid outlet line for generating, respectively, a first, a second, a third and a fourth pressure value;
- a second calculator programmed to calculate an inlet transmembrane value as the difference between the first and fourth pressure value and of an outlet transmembrane value as the difference between the second and third pressure value;
- a third calculator programmed to calculate an average transmembrane value between the inlet transmembrane value and the outlet transmembrane value;
- a fourth calculator programmed to calculate an actual permeability value as the ratio of the value of the first parameter and the average transmembrane value;
- a comparing device programmed to compare the inlet and outlet transmembrane values with respective threshold values;
- and a second controller programmed to control one of the first pumping apparatus and the second pumping apparatus and configured to alter one of the inlet flow of the liquid to be filtered and the controlled flow of the liquid component through the membrane when the inlet and outlet transmembrane values do not have respective permissible values.

15. A dialysis machine according to claim 9 wherein the first pumping apparatus comprises a first pump installed in the liquid inlet line, and the second pumping apparatus comprises a second pump installed in the dialysis fluid inlet line, a third pump installed in the dialysis fluid outlet line, and a fourth pump installed in a branch of the dialysis fluid outlet line, and said first controller controls the fourth pump.

16. A method for controlling a dialysis machine comprising the following steps:
- providing a filter having a first and a second compartment separated by a semi-permeable membrane;
- connecting to the first compartment a first circuit for a liquid including a liquid component, a cellular component that is retained by the membrane, and solutes that pass through the membrane;
- connecting to the second compartment a second circuit for a dialysis fluid;
- circulating the liquid to be filtered in the first compartment of the filter;
- causing a controlled flow of the liquid component and of the solutes through the membrane;
- determining a value of an ultrafiltration rate of the liquid component through the membrane;
- detecting a transmembrane pressure value across the membrane;
- calculating a value of the actual permeability as the ratio of the value of the ultrafiltration rate to the transmembrane pressure value;
- checking whether the actual permeability value satisfies a respective predetermined relation with respect to one or more threshold values; and,
- generating a signal indicating the result of the checking step.

17. A method according to claim 16, wherein the transmembrane pressure value detection step comprises the following sub-steps:
- determining pressure values at an inlet and an outlet of the first compartment and determining pressure values at an inlet and an outlet of the second compartment;
- calculating an inlet transmembrane value as the difference between the pressure value at the inlet of the first compartment and the pressure value at the outlet of the second compartment and an outlet transmembrane value as the difference between the pressure value at the outlet of the first compartment and the pressure value at the inlet of the second compartment; and
- calculating the transmembrane pressure value as an average transmembrane value between the inlet transmembrane value and the outlet transmembrane value.

* * * * *